(12) United States Patent
Sukkau et al.

(10) Patent No.: US 12,178,668 B2
(45) Date of Patent: Dec. 31, 2024

(54) MAGNETIC RESONANCE IMAGING SYSTEM AND METHOD FOR DETERMINING THE POSITION OF AT LEAST ONE COIL IN A MAGNETIC RESONANCE IMAGING

(71) Applicant: Siemens Healthineers AG, Forchheim (DE)

(72) Inventors: Johann Sukkau, Herzogenaurach (DE); Volker Matschl, Bamberg (DE); Steffen Schroeter, Fuerth (DE)

(73) Assignee: Siemens Healthineers AG, Forchheim (DE)

( * ) Notice: Subject to any disclaimer, the term of this patent is extended or adjusted under 35 U.S.C. 154(b) by 73 days.

(21) Appl. No.: 18/046,573

(22) Filed: Oct. 14, 2022

(65) Prior Publication Data

US 2023/0118471 A1 Apr. 20, 2023

(30) Foreign Application Priority Data

Oct. 19, 2021 (EP) ...................................... 21203537

(51) Int. Cl.
*A61B 90/00* (2016.01)
*A61B 5/055* (2006.01)
*G01R 33/34* (2006.01)
*G01R 33/48* (2006.01)

(52) U.S. Cl.
CPC .............. *A61B 90/39* (2016.02); *A61B 5/055* (2013.01); *G01R 33/34* (2013.01); *G01R 33/481* (2013.01); *A61B 2090/3933* (2016.02); *A61B 2090/3958* (2016.02)

(58) Field of Classification Search
CPC ............ A61B 90/39; A61B 2090/3933; A61B 2090/3958; A61B 5/055; G01R 33/34; G01R 33/481
See application file for complete search history.

(56) References Cited

U.S. PATENT DOCUMENTS 9,638,769 B2 5/2017 Wirtz et al.
2013/0165767 A1 6/2013 Darrow et al.
(Continued)

OTHER PUBLICATIONS

Lewerenz, M.: "Signalerhöhung durch Ultraschall in der Magnetresonanztomographie", Diplomarbeit, Mathematisch-Naturwissenschaftliche Fakultät der Rheinischen Friedrich-Wilhelms-Universität Bonn, Nov. 2007.
(Continued)

*Primary Examiner* — Chao Sheng
(74) *Attorney, Agent, or Firm* — Harness, Dickey & Pierce, P.L.C.

(57) ABSTRACT

At least one example embodiment provides a magnetic resonance imaging system comprising at least one local radiofrequency (RF) coil; and at least one marker element, wherein the magnetic resonance imaging system is configured to activate the at least one marker element and deactivate the at least one marker element such that the at least one marker element is detectable by the magnetic resonance imaging system at a position relative to the at least one local RF coil if the at least one marker element is activated, and the at least one marker element is not detectable by the magnetic resonance imaging system if the at least one marker element is deactivated.

20 Claims, 7 Drawing Sheets

(56) References Cited

U.S. PATENT DOCUMENTS

2014/0171784 A1 6/2014 Ooi et al.
2017/0065830 A1* 3/2017 Vahala ............... G01R 33/4808

OTHER PUBLICATIONS

Zijlstra F. et al.:"SMART tracking: Simultaneous anatomical imaging and real-time passive device tracking for MR-guided interventions", arXiv:1908.10769v1 [physics.med-ph] Aug. 28, 2019.
Oehms, O.B.: „Wechselwirkung des Kernspinsystems mit Ultraschall in einfachen Flüssigkeiten, Diplomarbeit, Mathematisch-Naturwissenschaftliche Fakultät der Rheinischen Friedrich-Wilhelms Universität Bonn, May 2006.
Eldib, M.; Bini, J. et al: "Attenuation Correction for MR Coils in Combined PET/MR Imaging: A Review", in: PET Clin. Apr. 2016 ; 11(2): 151-160. doi:10.1016/j.cpet.2015.10.004.

* cited by examiner

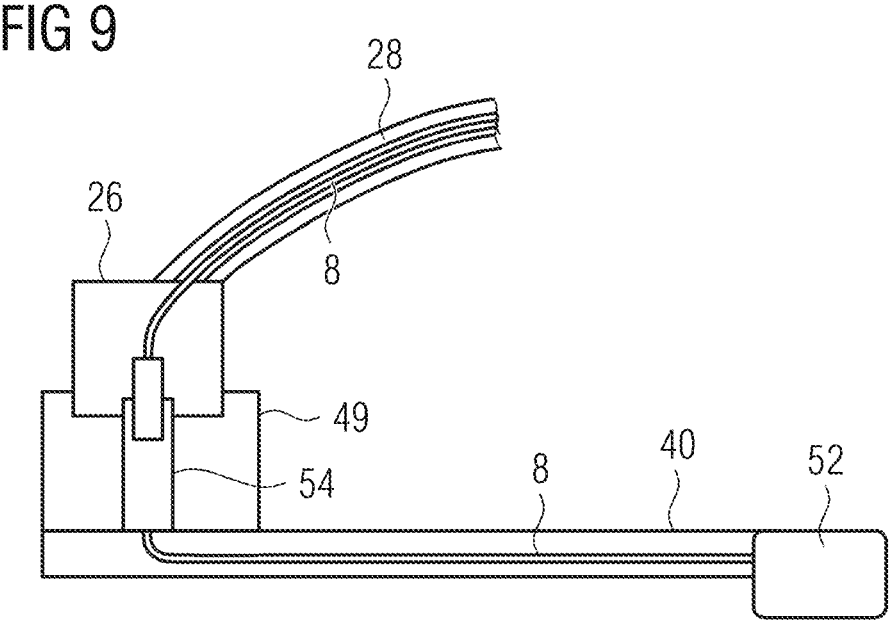
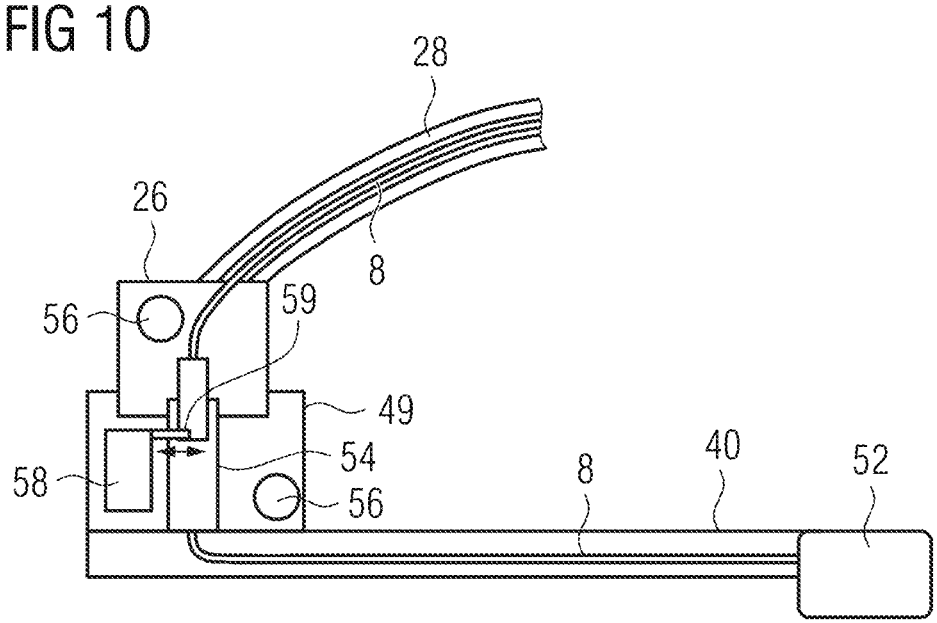

MAGNETIC RESONANCE IMAGING SYSTEM AND METHOD FOR DETERMINING THE POSITION OF AT LEAST ONE COIL IN A MAGNETIC RESONANCE IMAGING

CROSS-REFERENCE TO RELATED APPLICATION(S)

The present application claims priority under 35 U.S.C. § 119 to European Patent Application No. 21203537.2, filed Oct. 19, 2021, the entire contents of which are incorporated herein by reference.

FIELD

One or more example embodiments of the present invention concerns a magnetic resonance imaging system, in particular an MRI-PET system, and a method for determining the position of at least one coil in a magnetic resonance imaging.

State of the Art

Magnetic resonance imaging (MRI) systems are sometimes combined with another diagnostic system, such as a positron emission tomography (PET) system. These hybrid systems allow to acquire additional information, in particular without the need to reposition a patient in between different measurements, e.g. in between MRI and PET measurements. Hence it is possible to conduct examinations simultaneously or with only little time delay. This may be beneficial for some examinations, e.g. concerning cardiologic or neurological aspects. While providing two systems in one place can be beneficial, additional problems arise because of interferences between the different systems or between the components of the different systems. In particular, local radiofrequency (RF) coils of an MRI systems may disturb the measurement with another system. For example, a PET signal may be attenuated by local RF coils. This problem tends to increase when a lot of electronic components are comprised by the local RF coils of the MRT system.

In the state of the art, there are attempts to correct these attenuated signals after the measurement. One option is to generate an attenuation map of the coils, e.g. with a Computed Tomography (CT) scanner, in order to calculate and correct the attenuation of the PET signals. While those attenuation maps may be generated before the actual measurements, a problem arises with flexible surface coils which may be positioned more or less at any position on the patient. Hence the position of the local coils must be determined, possibly before each measurement. It has been proposed to use markers built into the coil in order to help detecting the coil via MRI or another measuring means, such as PET, infrared cameras or ultrasonic sensors. However, none of these solutions has been successfully implemented yet without giving rise to further disadvantages. In particular, markers that are detectable by MRI have the disadvantage that they are also visible during an MRI examination. This may lead to false or less reliable diagnoses, e.g. due to aliasing artefacts.

For example, Eldib et al.: "Attenuation Correction for MR Coils in Combined PET/MR Imaging: A Review"; pet Clin: Author manuscript; available in PMC 2017 Apr. 1, describe the concept of a markers-based localization. However, they come to the conclusion that the current implementation is not an ideal technique due to the interference of the these "fiducial markers" with the MR images.

SUMMARY

One or more example embodiments of the present invention provide an MRI, in particular a hybrid MRI system, wherein the problem of local coils being in the way of a measurement with another measurement method, in particular PET, can be accounted for without significantly disturbing the MRI measurement.

At least one example embodiment provides a magnetic resonance imaging system comprising at least one local radiofrequency (RF) coil; and at least one marker element, wherein the magnetic resonance imaging system is configured to activate the at least one marker element and deactivate the at least one marker element such that the at least one marker element is detectable by the magnetic resonance imaging system at a position relative to the at least one local RF coil if the at least one marker element is activated, and the at least one marker element is not detectable by the magnetic resonance imaging system if the at least one marker element is deactivated.

According to one or more example embodiments, the at least one marker element comprises a magnetic resonance visible fluid, and the magnetic resonance visible fluid has a magnetic resonance repetition time below 1000 ms.

According to one or more example embodiments, the imaging system further includes a relocation system configured to relocate the at least one marker element with respect to at least one of the at least one local RF coil or the magnetic resonance imaging system, deactivate the at least one marker element by removing the at least one marker element from at least one of the at least one local RF coil or a field of view of the magnetic resonance imaging system, and activate the at least one marker element by moving the at least one marker element.

According to one or more example embodiments, the relocation system comprises a fluid conducting element containing the magnetic resonance visible fluid, the fluid conducting element including a first part and a second part, the first part being at the at least one local RF coil or within the at least one local RF coil and the second part being outside of a detectable area of the magnetic resonance imaging system, and a fluidic pump configured to move the magnetic resonance visible fluid from the first part into the second part and vice versa.

According to one or more example embodiments, the at least one local RF coil comprises at least one ceramic element around at least one electronic component of the at least one local RF coil, the at least one ceramic element comprises at least one fluid channel connected to the fluid conducting element, the magnetic resonance visible fluid is a cooling fluid, and the fluidic pump is configured to move the magnetic resonance visible fluid through the at least one fluid channel.

According to one or more example embodiments, the imaging system further includes a cable mechanism configured to activate the at least one marker element and deactivate the at least one marker element.

According to one or more example embodiments, the imaging system further includes a hauling mechanism configured to move the at least one marker element at least one of with respect to the at least one local RF coil or in and out of a detectable area to activate the at least one marker and deactivate the at least one marker.

According to one or more example embodiments, the hauling mechanism comprises a movable cable extending from the at least one local RF coil to an area outside of the detectable area of the magnetic resonance imaging system, wherein the at least one marker element is attached to the movable cable such that the at least one marker element is movable between the at least one local RF coil and the area outside of the detectable area of the magnetic resonance imaging system via the movable cable.

According to one or more example embodiments, the at least one marker element is a capsule containing a magnetic resonance visible fluid.

According to one or more example embodiments, the imaging system further includes a shielding element, at least one of (i) the shielding element being movable into a shielding position and into a non-shielding position or (ii) the at least one marker element being movable into a shielding position and into a non-shielding position, wherein the shielding element encloses the at least one marker element such that the at least one marker element is shielded from the magnetic resonance imaging system when at least one of the shielding element or the at least one marker element is in the shielding position, and the shielding element is apart from the at least one marker element such that the at least one marker element is detectable by the magnetic resonance imaging system when at least one of the shielding element or the at least one marker element is in the non-shielding position.

According to one or more example embodiments, the shielding element is a tube.

According to one or more example embodiments, the imaging system further includes an air pressure chamber; and a fluid conducting element connected to the air pressure chamber, wherein the shielding element and the at least one marker element are inside the air pressure chamber, and the shielding element is movable by air pressure provided via the fluid conducting element.

According to one or more example embodiments, the imaging system further includes a cable mechanism, wherein the cable mechanism is configured to move the shielding element from the shielding position to the non-shielding position and vice versa.

According to one or more example embodiments, the imaging system further includes an ultrasound emitter, wherein the ultrasound emitter is configured to provide ultrasound waves at the at least one marker element to deactivate the at least one marker element with the ultrasound waves.

According to one or more example embodiments, a method for determining the position of the at least one local RF coil of the magnetic resonance imaging system, the method comprising providing the at least one marker element at the position relative to the at least one coil in the activated state; taking a magnetic resonance measurement with the magnetic resonance imaging system while the at least one marker element is activated to obtain first test data; determining the position of the at least one marker element to determine the position of the at least one coil based on the first test data; and deactivating the at least one marker element for further measurements.

BRIEF DESCRIPTION OF THE DRAWINGS

Embodiments of the invention are now described with reference to the attached figures. Similar or corresponding components are designated with the same reference signs.

FIG. 9 shows a fluid plug connected to a tube connector according to an embodiment of the invention, FIG. 10 shows a fluid plug connected to a tube connector according to another embodiment of the invention.

DETAILED DESCRIPTION

Figure 1:
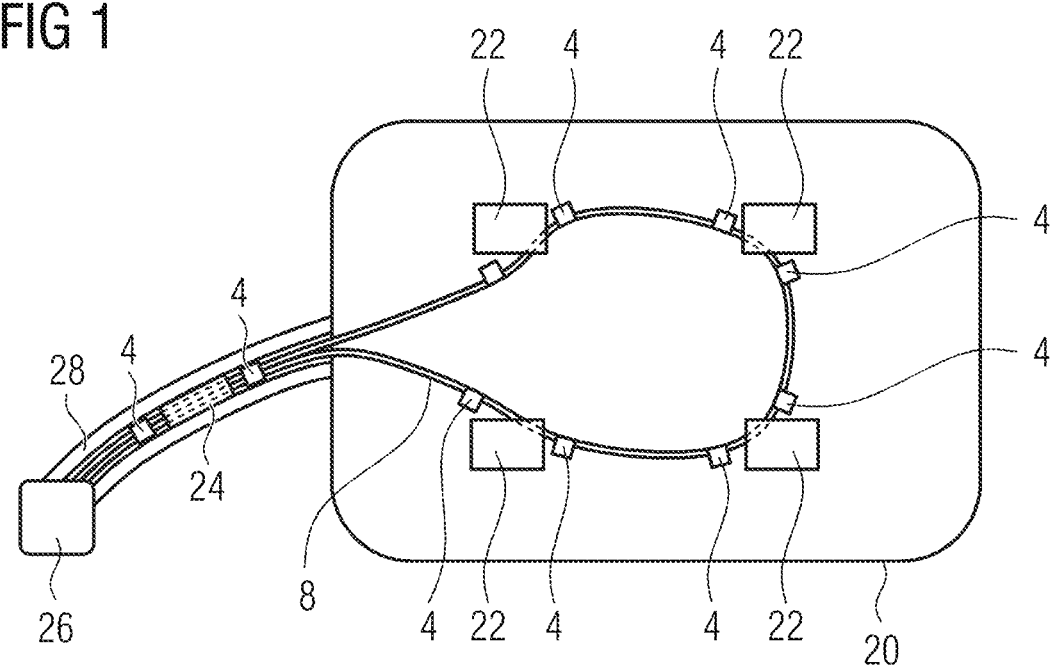
FIG. 1 shows a schematic representation of a local RF coil with several marker elements according to an embodiment of the invention.

According to one or more example embodiments of the present invention, a magnetic resonance imaging system (MRI), in particular an MRI-PET system, is provided. The magnetic resonance imaging system comprises at least one local RF coil and at least one marker element, wherein the magnetic resonance imaging system and the marker element are configured such that the at least one marker element may be activated to be detectable by the magnetic resonance imaging system at a predetermined position relative to the coil, wherein the magnetic resonance imaging system and the marker element are configured such that the at least one marker element may be deactivated not to be detectable by the magnetic resonance imaging system. The MRI system may preferably be a hybrid MRI system. In particular, an MRI system may be combined with a positron emission tomography (PET) system. A "local RF coil" is in particular a receive coil or receive/transmit coil, which is not integrated into the bore of the MRI main magnet, but which is placed close to the body part to be examined just before the MRI examination. The local RF coil is often interchangeable, depending on the body part to be examined. In the context of this invention the local RF coil may also be referred to as "coil". The coil may be a flexible surface coil, which can be placed at various regions with respect to the MRI scanner and/or the patient. Advantageously, the marker element may allow to determine the position of the coil and thus to predetermine its influence on the measurement of another measuring system, e.g. the PET system. In the case of a PET system, the attenuation effect of the coils (the position of which is determined via the marker element) on a PET measurement may be calculated in order to subtract this effect from the data and/or adjust the PET measurement accordingly. A review of methods to apply such an attenuation correction in the case of MRI-PET systems is described for example in Eldib et al.: "Attenuation Correction for MR Coils in Combined PET/MR Imaging: A Review"; pet Clin: Author manuscript; available in PMC 2017 Apr. 1.

The MRI system is in particular configured to determine the position of the at least one coil based on the activated marker element, in particular by taking an MR image of a scan area including the marker element. Preferably, during this measurement the coil and relative to it the marker element, i.e. placed in a predetermined position relative to the coil, may be placed in essentially the same position as later during a diagnostic measurement. The marker element may for example be attached to the coil, integrated into the coil and/or be arranged at least partially around the coil. In contrast to the state of the art, the inventive system takes care of the problem that the marker element might influence an examination via the MRI system by providing a marker element that can be deactivated. The MRI system may preferably be configured to deactivate the marker element prior to executing a diagnostic MRI measurement. Thus, the marker element will not or will barely have any influence on the MRI diagnostic measurement due to being invisible to the MRI scanner. The MRI system may be configured to automatically deactivate the marker element and/or to deactivate the marker element based on user input. The marker element may for example be deactivated by removing it from the coil and/or the MR field of view, by shielding it against high frequency radiation and/or by destroying the phase coherence of the signal of an MR visible substance of the marker element.

According to an embodiment, the marker element may comprise a magnetic resonance (MR) visible substance, such as a magnetic resonance visible fluid, in particular liquid, and/or a magnetic resonance visible solid substance. Preferably, the visible substance, in particular fluid, may have a low magnetic resonance repetition time, TR, TR being in particular below 1000 ms, preferably in the range from 50 ms to 1000 ms, more preferably in the range from 100 ms to 1000 ms. The MR visible substance may for example comprise water, an aqueous solution, silicone, synthetics, or a gas such as xenon or fluor. A low TR may be particularly advantageous, since it may enable fast T1 weighted MR imaging. Thus, a measurement for the localisation of the at least one coil can be relatively fast, i.e. the time needed for non-diagnostic scans may be short. The solid substance may preferably be soluble in an imaging fluid, such as water, have a low TR and/or have a high susceptibility. For example, the solid substance may be or may comprise a lanthanide, in particular Gadolinium. Gadolinium is also commonly used in MR contrast agents. However, the marker element may also comprise a water solution containing another substance. Possible substances may for example be a compound containing iron, such as iron sulphate iron chloride, iron bromide, iron iodide, iron nitrate, chemical compounds containing nickel, cobalt and/or chromium such as chromium sulphate, chromium chloride, nickel sulphate and/or cobalt sulphate, and/or non-metal compounds, in particular salts, such as neodymium sulphate. Iron sulphate, for example, may be cheaper than Gadolinium while advantageously providing comparable results concerning MR contrast for fast 3D MR measurements, due to having a comparable susceptibility. The susceptibility may be adapted by varying the concentration of the substance, in particular iron sulphate, in the water solution, i.e. between 0 and saturation at 256 g/l at 20° C. for iron sulphate. In particular the concentration may be adapted with respect to image contrast, needing high concentration, and low magnetic flux (BO) distortion close to the marker element, needing low concentration.

According to an embodiment, the magnetic resonance imaging system may comprise a relocation system configured to relocate the marker element with respect to the coil and/or the magnetic resonance imaging system, wherein the relocation system is configured to deactivate the marker element by removing it from the coil and/or from the field of view of the magnetic resonance imaging system and to activate the marker element by moving it to a predetermined position in the proximity of the coil or inside the coil. In particular the system may be configured to remove the marker element prior to a diagnostic MR scan. The relocation system may comprise a cable mechanism and/or a fluid pump system configured to relocate the marker element. Advantageously, the relocation system may allow to provide a way of removing the marker element from the field of view of the MRI system and thus ensuring that it is undetectable by the MRI system. Hence, the marker element may be deactivated with respect to the MRI system by removing it from the area to be imaged.

Advantageously, the relocation system may comprise a fluid conducting element, in particular a tube, and a fluidic pump, wherein the marker element comprises a magnetic resonance (MR) visible fluid, in particular liquid, wherein the fluid conducting element is configured such that a first part of the fluid conducting element is arranged at or within the coil and a second part of the fluid conducting element is arranged outside of the detectable area of the magnetic resonance imaging system, wherein the fluidic pump is configured to move the magnetic resonance visible fluid from the first part into the second part and vice versa. The fluid conducting element, in particular its second part, may at least partially be positioned within a patient table of the MRI system. The second part may preferably be positioned at least 50 cm outside of the iso center of the MRI system. In particular, the second part may, for example, be positioned at the foot end of the patient table. The first part of the fluid conducting element may be positioned close by all components of the coil and optionally of other components outside the coil which are relevant with respect to the attenuation of PET signals. Relevant components may for example be at least one pre-amplifier and/or at least one braid-breaker. The MR visible fluid may be a fluid and/or a solution as described above. The fluidic pump may be configured to move the MR visible fluid based on overpressure (positive pressure) and/or underpressure (negative pressure). The fluid conducting element may at least partially be filled with the MR visible fluid. In this case the marker element may comprise the MR visible fluid along its whole distribution within the fluid conducting element. The marker element in the form of the MR visible fluid may appear as a 3D network marking all relevant components of the coil and/or attached to the coil. The 3D network may for example have the shape of a spiral or a meandering shape or any other shape which is expedient to mark the relevant components. Alternatively, the MR visible fluid may be contained in at least one capsule, in particular a capsule as described below, preferably a plurality of capsules, which are positioned inside the fluid conducting element. The fluid conducting element may further contain a guiding fluid, e.g. compressed air with positive and/or negative pressure. The pump may be configured to move the at least one capsule via manipulation of the guiding fluid, wherein the pump may in particular push and/or pull the at least one capsule within the fluid conducting element via the guiding fluid in between the first and the second part of the fluid conducting element.

According to an embodiment, the system may comprise a tube connector. An outside part of the fluid conducting element, in particular comprising the first part, may be attached to the coil and comprise a fluid plug, wherein the fluid plug is configured to be plugged into the tube connector. Preferably, the tube connector may comprise a locking means, configured to lock the tube connector to the fluid plug, in particular when fluid is in the first part of the fluid conducting element. The locking means may comprise a bolt configured to lock the tube connector and the fluid plug. The system, in particular at the tube connector and/or at the fluid plug, may comprise an activating means, e.g. a push button, wherein the system is configured, as a reaction to the push button being pushed, to activate the fluidic pump such that the MR visible fluid is pumped out of the outside part of the fluid conducting element and the locking means is unlocked afterwards such that the fluid plug can be unplugged. Advantageously the locking means can thus prevent leakage of fluid when disconnecting the outside part of the fluid conducting element. The tube connector and/or the fluid plug may comprise a connecting valve, configured to prevent leakage of fluid when the tube connector and the fluid plug are not connected to each other.

According to an embodiment, the coil may comprise at least one ceramic element arranged around at least one electronic component of the coil, wherein the ceramic element may comprise at least one fluid channel connected to the fluid conducting element, wherein the magnetic resonance visible fluid is configured to work as a cooling fluid, wherein the fluidic pump is configured to move the magnetic resonance visible fluid through the at least one fluid channel. The fluid channel may be considered to be part of the fluid conducting element. Thus "connected to the fluid conducting element" may be interpreted to mean "connected to the part of the fluid conducting element not being part of the fluid channel of the ceramic element". In particular the fluid channel may be the first part or a portion of the first part of the fluid conducting element. Preferably the ceramic element is thermally conductive. The ceramic element may for example be made of at least epoxy resin and ceramic powder. The ceramic powder may comprise aluminium nitride, boron nitride and/or silicon carbide. Such a ceramic element may, for example have a thermal conductivity of up to about 30 W/mK. Alternatively, the ceramic element may be a sintered ceramic form. The thermal conductivity may thus reach up to about 300 W/mK. The at least one electronic component may be an electronic board, a pre-amplifier, a diode, in particular PET diode, an electronic choke and/or a capacitor. Advantageously, the MR visible fluid may thus also serve as a cooling agent. The system may for example be configured to apply a cooling process via the MR visible fluid running through the fluid channel of the ceramic element in measurement breaks and/or during localisation of the coil position via the MR visible fluid. In addition, the ceramic element may serve to improve the PET imaging. Electronic components, due to having high electron densities and small overall sizes often appear as sharp and highly visible spots in a PET image. Due to the ceramic element, the electron density in between the components is also increased and thus spots will advantageously appear less sharp as compared to an embodiment without the ceramic element. Instead, a uniform background may be created, which does not disturb the overall PET image as much as single sharp spots. According to a preferred embodiment, the edge areas of the ceramic element may be thinner than the central area of the ceramic element. This may lead to the electron density decreasing towards the edge of the ceramic element, further leading to less pronounced edges in the PET image. At least one temperature sensor may be located at the at least one component and/or at blocks of components and/or at the ceramic element. The system may be configured to control a cooling process of the electronic component(s) using the temperature sensor.

According to an embodiment, the imaging system may comprise a cable mechanism configured to activate and deactivate the at least one marker element. The cable mechanism may be configured to pull the marker element in and out of the field of view of the MRI scan area. Alternatively, the cable mechanism may be configured to move a shielding element which is configured to shield the marker element from a shielding position to a non-shielding position and vice versa. The system comprising the cable and/or hauling mechanism according to any embodiment described herein may further comprise a tube through which the cable and/or the marker elements are guided. The tube may preferably be flexible, e.g. be a hose. The tube may be separable and connectable, wherein a coil portion of the tube is attached to the coil and a base portion comprises a cable connector, wherein the coil portion comprises a cable plug connectable or connected to the cable connector. The cable may be separable into two parts, wherein the two parts are connectable to each other. For example, both parts may comprise hooks configured to enable a connection of the two parts. The system may be configured to enable a separation of the tube portions, wherein one part of the cable may remain in the coil portion of the tube and the other part of the cable may remain in the base portion when the tube parts are disconnected from each other.

According to an embodiment the imaging system may comprise a hauling mechanism, in particular a cable mechanism, wherein the hauling mechanism is configured to move the at least one marker element with respect to the coil and/or in an out of the detectable area of the magnetic resonance imaging system in order to activate and deactivate the at least one marker. Preferably, the hauling mechanism may comprise a movable cable extending from the coil to an area outside of the detectable area of the magnetic resonance imaging system, wherein the at least one marker element is attached to the cable such that it can be moved between the coil and the area outside of the detectable area of the magnetic resonance imaging system via the cable. Preferably, a plurality of marker elements may be attached to the cable. Different marker elements may be configured to mark different electronic components of the coil, in particular at a predetermined distance with respect to each other. The cable may consist of polyamide fibres, preferably synthesized polyamide fibres, more preferably aramid fibres. The cable may comprise a first part onto which marker elements, in particular capsules containing an MR visible fluid, are attached, and a second part onto which no marker elements are attached to. The system may be configured to activate the marker elements by pulling the first part of the cable into or at a position adjacent to the coil and to deactivate the marker elements by pulling the first part of the cable to the area outside of the detectable area of the magnetic resonance imaging system. In a deactivated state of the marker elements, the second part of the cable may be positioned at and/or in the coil. The hauling mechanism may partially be located inside the patient table, in particular the area outside the detectable are of the MRI system may at least partially be inside the patient table. The cable may be separable into two parts, in particular the first part and the second part, wherein the two parts are connectable to each other.

According to an embodiment, the MRI system may comprise an MR compatible motor configured to drive the cable mechanism and/or the hauling mechanism as described herein. An MR compatible motor is in particular a motor that can be used while a magnetic field created by the MRI system is activated. The motor may be built into the patient table. The MRI system may further comprise a control unit configured to control the MR compatible motor.

According to an embodiment, the at least one marker element may be a capsule containing a magnetic resonance (MR) visible fluid, in particular liquid. The capsule may be attached to the cable of the cable mechanism. The capsule may be made of glass and/or plastic. The capsule may have the shape of an ellipsoid or of a cuboid, in particular a rectangular cuboid, or of a cylinder. The capsule may have a diameter of 1 mm to 20 mm and a length of about 1 mm to 50 mm. The MR visible liquid may in particular be the MR visible liquid as described above. A capsule may be an easy and reliable way of providing an MR visible fluid for a marker element, which may in particular be flexible with respect to the arrangement and positioning of the fluid.

According to an embodiment, the magnetic resonance imaging system may comprise a shielding element, wherein the shielding element is adjustable, in particular movable and/or activatable, in such a way that it can be in a shielding mode to shield the marker element from RF radiation and/or from detection by the magnetic resonance imaging system and be in a non-shielding mode to allow detection of the marker element by the magnetic resonance imaging system and/or such that the marker element is not shielded from RF radiation. The MRI system may be configured to activate the shielding element during a diagnostic scan. The marker element may be fixed at its position, in particular within the coil. The shielding element may be made of carbon fibres. This may be advantageous compared to other options such as the shielding element being made of copper, since copper or other metals tend to enable eddy currents and have strong PET damping properties. Carbon fibres, on the other hand, tend to be mostly transparent for PET measurements and have no significant eddy currents compared to eddy currents in metals. The shielding element may be a tube and/or have the shape of a tube. Preferably the shielding element may have the same geometrical shape as the marker element, wherein the inner diameter and/or inner volume is greater than the outer diameter and/or outer volume of the marker element. The shielding element may have a wall thickness no more than 1 mm, in particular of 0.01 mm to 1 mm, preferably of 0.1 mm to 1 mm. Advantageously, a shielding element with such a thickness may be basically transparent with respect to PET measurements.

According to a preferred embodiment, the shielding element may permanently enclose the marker element and be activatable, wherein the shielding element is configured such that it shields the marker element when it is activated and does not shield the marker element when it is deactivated. The shielding element may be installed immovably around the marker element and/or inside or around the coil. The shielding element may be configured such that its RF damping is electronically controllable. The MRI system may comprise a control unit configured to control the RF damping of the shielding element electronically. The shielding element may comprise at least one temperature-dependent resistor, preferably a plurality of temperature-dependent resistors, in particular a negative temperature coefficient thermistor or a positive temperature coefficient thermistor. In particular a network of temperature-dependent resistors may be arranged around the marker element. The conductivity of the shielding element may be controlled via controlling the temperature of the temperature-dependent resistor and/or of the shielding element. The MRI system may comprise a heating element, in particular made from carbon, and/or a cooling circuit configured to control the temperature of the temperature-dependent resistor and/or of the shielding element.

According to another preferred embodiment, the magnetic resonance imaging system may comprise a, in particular movable, shielding element, wherein the shielding element is movable in such a way that it can be moved into a shielding position and into a non-shielding position and/or wherein the marker element is movable in such a way that it can be moved into a shielding position and into a non-shielding position, wherein the shielding element encloses the marker element such that the marker element is shielded from the magnetic resonance imaging system and/or from RF radiation when the shielding element and/or the marker element is in the shielding position, and wherein the shielding element is apart from the marker element such that the marker element is detectable by the magnetic resonance imaging system and/or not shielded from RF radiation when the shielding element and/or the marker element is in the non-shielding position. The shielding element may in particular be slidable over the marker element and/or the marker element may be slidable into the shielding element. Using a shielding element may in particular be advantageous since no PET visible components and no electronic components or electronic lines need to be used. Thus, the shielding element may be neutral with respect to magnetic resonance measurements as well as to PET measurements. The range of movement of the shielding element and/or of the marker element may correspond to and/or be essentially equal to the length of the marker element in the direction of movement of the shielding element and/or marker element. The shielding element may be dimensioned such that its inner dimensions are slightly larger than the outer dimensions of the marker element, in particular such that there is a gap of about 0.1 mm to 0.5 mm between the shielding element and the marker element when the shielding element encloses the marker element.

According to an embodiment, the magnetic resonance imaging system may comprise an air pressure chamber and a fluid conducting element, in particular an air hose or air tube, connected to the air pressure chamber, wherein the shielding element and the marker element are arranged inside the air pressure chamber, wherein the air pressure chamber and the shielding element are configured such that the shielding element is movable by air pressure provided via the fluid conducting element. The MRI system may comprise a pump and a control unit configured to control the air pressure inside the fluid conducting element and the air pressure chamber. The control unit may be configured to control the air pressure such that the marker element is shielded and thus deactivated during a diagnostic scan and non-shielded and thus activated for determining the position of the coil. The control unit and the pump may be configured to control movement of the shielding element by providing overpressure and/or underpressure inside the air pressure chamber via the fluid conducting element. For example, moving the shielding element over the marker element may be achieved by overpressure while moving the shielding element away from the marker element may be achieved by underpressure or vice versa. The air pressure chamber may comprise a first portion and a second portion. An air inlet connected to the fluid conducting element may be arranged in the first portion. An air outlet may be arranged in the second portion. Preferably the shielding element may at least partially be arranged inside the air pressure chamber movably in between the air inlet and the air outlet and/or in between the first portion and the second portion. The shielding element and the air pressure chamber may be configured such that positive air pressure in the first portion pushes the shielding element towards the second portion and over the marker element. The marker element may be positioned in the second portion and/or at any position suitable to allow pushing the shielding element over the marker element via the air pressure. The shielding element and the air pressure chamber may be configured such that negative air pressure in the first portion pulls the shielding element back towards the first portion and away from the marker element. Equivalently, the shielding element and the air pressure chamber may be configured such that positive air pressure in the first portion pushes the shielding element towards the second portion and away from the marker element. The marker element may thus be positioned in the first portion and/or at any position suitable to allow pushing the shielding element away from the marker element via the air pressure. The shielding element and the air pressure chamber may be configured such that negative air pressure in the first portion pulls the shielding element back towards the first portion and over the marker element. The air outlet may be configured to balance the air pressure in the second portion, in particular when the shielding element is moved. According to an alternative embodiment, the shielding element may be fixed and the marker element may be movable via air pressure according to the above description. According to a further embodiment, both the marker element and the shielding element may be movable, in particular towards and away from one another, according to the above description.

Preferably the MRI system may further comprise a tube connector and a fluid plug, in particular as described above. The tube connector may comprise an air socket and the fluid plug may be configured to engage with the air socket such that no or only little compressed air is lost. A locking means as described above is an option here as well. However, it may not be necessary for this embodiment, since the used pressure may be relatively low and further security measures may thus not be required.

According to an embodiment, the magnetic resonance imaging system may comprise a cable mechanism, wherein the cable mechanism is configured to move the shielding element from the shielding position to the non-shielding position and/or vice versa. The cable mechanism may comprise a cable, in particular made of aramid fibre, which is connected to the shielding element. The cable mechanism may comprise a tube or hose, in particular made of plastic, within which the cable is guided. The cable according to one or more example embodiments of the present invention may in particular be a rope or pull rope. The MRI system may further comprise a spring, in particular a non-magnetic spring, configured to move the shielding element to the shielding position or to the non-shielding position. Accordingly, the cable mechanism may be configured to move the shielding element against the force of the spring. For example, the spring may pretension the shielding element in the shielding position and the cable mechanism may be configured to pull the shielding element into the non-shielding position when the position of the coil is to be determined. The cable mechanism may comprise an MR compatible motor, in particular as described above, a rotary shaft driven by the motor, an eccentric connected to the rotary shaft, a bolt movable by the eccentric, and a lever movable by the bolt. The eccentric may be configured such that a rotation of the rotary shaft drives the bolt which in turn flips the lever and a further rotation drives the bolt further such that the lever flips back. The lever may be connected to the cable in such a way that flipping the lever pulls the cable and thus pulls the shielding element connected to the cable while flipping the lever back loosens the cable, in particular enabling the spring to pull the shielding element back into its original position.

According to an embodiment, the magnetic resonance imaging system may comprise an ultrasound emitter, wherein the ultrasound emitter may in particular be arranged adjacent to the marker element, wherein the ultrasound emitter is configured to provide ultrasound waves at the marker element in order to deactivate the marker element with the ultrasound waves, in particular by destroying phase coherence in the marker element. It has been shown that ultrasound waves can influence the nuclear spin and MRI (Meinert Lewerenz: "Signalerhohung durch Ultraschall in der Magnetresonanztomographie", Diplomarbeit, Mathematisch-Naturwissenschaftliche Fakultat der Rheinischen Friedrich-Wilhelms-Universitat Bonn, November 2007 and Ole Benjamin Oehms: "Wechselwirkung des Kernspinsystems mit Ultraschall in einfachen Flüssigkeiten", Diplomarbeit, Mathematisch-Naturwissenschaftliche Fakultat der Rheinischen Friedrich-Wilhelms Universität Bonn, Mai 2006). In particular, using an appropriate frequency of ultrasound waves may destroy the MR phase coherence of the spins. Accordingly, ultrasound waves may temporarily turn the marker element invisible for MRI. The ultrasound emitter may for example comprise a piezo crystal. The MRI system may comprise a control unit configured to control the ultrasound emitter. This control unit and other control units described herein may be the same control unit or may be different control units. The control unit may be connected to the ultrasound emitter via at least one control line, preferably two control lines. Additionally or alternatively, the ultrasound emitter may be digitally controlled via an inter-integrated circuit (I2C) and/or a serial peripheral interface (SPI).

According to an embodiment the MRIs system may further comprise at least one additional marker element and at least one braid-breaker, wherein the braid-breaker is in particular positioned along a connecting cable of the coil, wherein the magnetic resonance imaging system and the marker element are configured such that the at least one additional marker element may be activated to be detectable by the magnetic resonance imaging system at a predetermined position relative to the braid-breaker, wherein the magnetic resonance imaging system and the additional marker element are configured such that the at least one additional marker element may be deactivated not to be detectable by the magnetic resonance imaging system. A braid-breaker is in particular a shielding element that shields of the MR signal from the marker element. The braid-breakers may comprise a RF shield. Preferably the system may comprise a plurality of braid-breakers and a plurality of corresponding marker elements. More preferably the system may comprise two marker elements for each braid-breaker, wherein the marker elements may in particular be positioned on opposite sites adjacent to the braid-breaker, preferably before and behind the braid-breaker along the cable of the coil. The braid-breakers may for example be positioned at the cable at intervals of 20 to 40 cm. It is also conceivable to provide the at least one additional marker element for the at least one braid-breaker independently of the at least one marker element for the coil. Braid-breakers usually have a relatively high electron density, which may lead to a strong PET damping. This embodiment may thus allow to determine the position of the at least one braid-breaker along the cable of the coil. The RF shield of the at least one braid-breaker may be made of carbon fibre. This may be advantageous since a braid-breaker made of carbon is less visible for PET (though usually still visible due to its thickness) than usual braid-breaker materials, such as copper, while still being able to providing RF shielding.

According to one or more example embodiments of the present invention, a method for determining the position of at least one coil in a magnetic resonance imaging system, in particular the magnetic resonance imaging system as described herein, is provided. The magnetic resonance imaging system comprises a marker element that is detectable by the magnetic resonance imaging system, the at least one coil and preferably a control unit. The control unit may be configured to control the activation and/or deactivation of the marker element. The method comprises the steps:

providing the marker element at a predetermined position relative to the at least one coil in an activated state,
taking a magnetic resonance (MR) measurement with the magnetic resonance imaging system while the marker element is activated in order to obtain first test data,
determining the position of the at least one coil and thereby the position of the at least one coil based on the first test data, in particular at the control unit, and
deactivating the marker element for further measurements.

All features and advantages of the system may be adapted to the method and vice versa. The MR measurement for obtaining first test data may be carried out using fast gradient echo sequences. The method may comprise detecting further components such as braid-breakers analogously to the detection of the coil. The position of the at least one coil may be determined by using coordinates, in particular 3D coordinates, of the marker elements from the first test data. The marker elements may in particular be visible as a bright spot in the MR image of the first test data which shows the position of the marker element within the field of view of the MRI system. The position of the marker element based on the test data may be determined automatically and/or by allowing input of a user. The position of the coil may thus be derived via the position of the marker element due to a known spatial relation between the marker element and the coil. In a further step, an attenuation correction may be carried out according to the state of the art, in particular for PET data, with the determined position of the coil.

According to an embodiment, the method may comprise the further steps:

taking a magnetic resonance measurement with the MRI system when the marker element is deactivated in order to obtain second test data, wherein in particular all other parameters are unchanged with respect to the measurement of the activated marker element,
subtracting the second test data from the first test data in order to obtain adjusted data, in particular at the control unit, and
determining the position of the at least one marker element and thereby the position of the at least one coil based on the adjusted data instead of the first test data.

This embodiment may have the advantage that in the adjusted data, essentially only the signal of the marker element is visible (in particular as bright voxels within an otherwise dark 3D MR image). Accordingly, the determination of the position of the marker element may be particularly easy.

FIG. 1 shows a schematic representation of a local RF coil 20 with several marker elements 4 according to an embodiment of the invention. The marker elements 4 may for example be capsules containing an MR visible fluid. The local RF coil 20 comprises a coil cable 28 with a fluid plug 26 which can be connected to tube connector 49 (not shown here). The coil cable 28 is configured to connect the coil 20 to a control unit 64 (not shown here) of the system. A fluid conducting element 8 is leading through the coil cable 28 and passing several electronic components 22. The fluid conducting element 8 may be connected to a source of air pressure or to another part of the fluid conducting element 8 filled, for example, with MR visible fluid, which may be pumped through the fluid conducting element, via the tube connector 49. The marker elements 4 may either be fixed at their position or they can be moved along the fluid conducting element 8, for example by air pressure. If the marker elements 4 are fixed at their position they may for example be activated and deactivated by shielding elements 12 (not shown here) which may for example be moved over the marker elements 4 via air pressure guided through the fluid conducting element 8. The electronic components 22 of the coil 20 can influence the imaging of other imaging methods carried out in parallel or consecutively to the MRI. For example, they may attenuate the signal of PET scans. It is therefore useful to correct this attenuation by calculating the effect of attenuation and adjusting the (PET) image data accordingly. For this, it is necessary to determine the position of the movable coil 20 and its components 22. Since the marker elements 4 are or can be positioned at predetermined positions with respect to the electronic components 22 of the coil 20 and since the marker elements 4 are highly visible in MRI images when activated they can be used to determine the position of the coil 20 and of the electronic components 22 of the coil 20. In the coil cable 28 there is at least one braid-breaker 24 which can also influence measurement signals such as a PET signal. According to this embodiment, the position of the braid breaker can also be determined via two marker elements 4 which are placed before and after the braid breaker 24 inside the coil cable 28.

Figure 2:
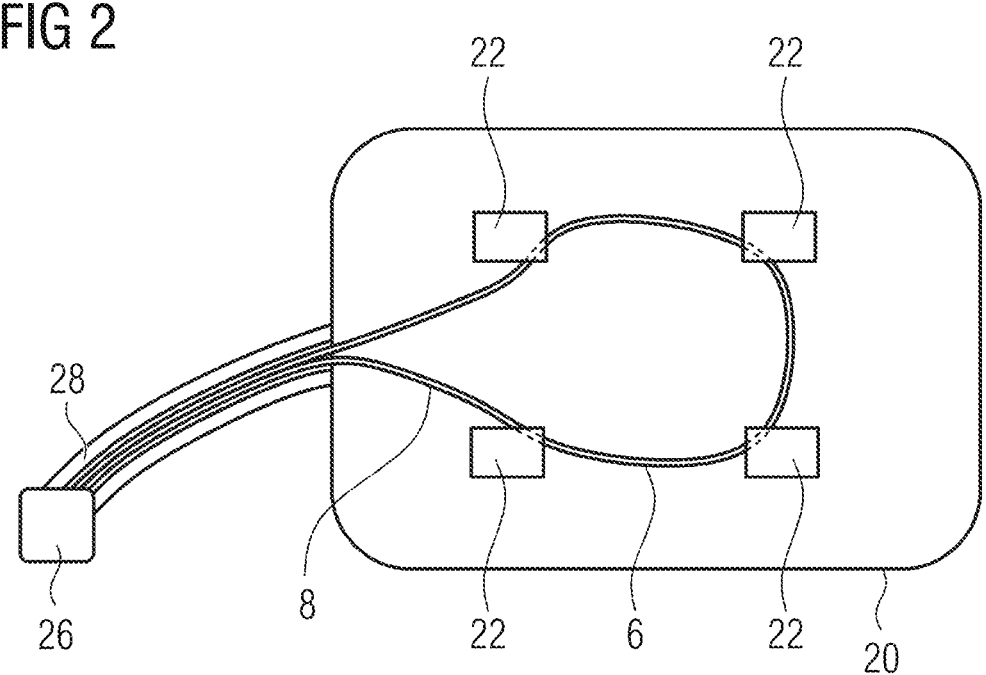
FIG. 2 shows a schematic representation of a local RF coil with a fluid conducting element according to another embodiment of the invention.

FIG. 2 shows a schematic representation of a local RF coil 20 with a fluid conducting element 8 according to another embodiment of the invention. In this embodiment, the marker element 4 is an MR visible fluid 6 which is pumped through the fluid conducting element 8. The MR visible fluid 6 can be pumped into and out of the fluid conducting element 8 inside the coil 20 and the coil cable 28 via the fluid plug 26 which can be connected to a corresponding tube connector 49. When the MR visible fluid 6 is inside the coil 20 and thus the marker element 4 is activated, it will appear as a bright network in an MR image which can be used to determine the position and orientation of the coil 20. Thereby, the fluid conducting element 8 is guiding the MR visible fluid 6 around the electronic components 22 of the coil 20. Hence it is possible to specifically determine the location of these components 22 as derived from the position and orientation of the fluid conducting element 8 filled with the MR visible fluid 6. In order to carry out MRI scans, the MR visible fluid 6 is pumped out of the part of the fluid conducting element 8 that is inside the coil 20 and, via the fluid plug 26, into a part not inside the field of view of the scanner (not shown) and thus it does not disturb the MR imaging process.

Figure 3:
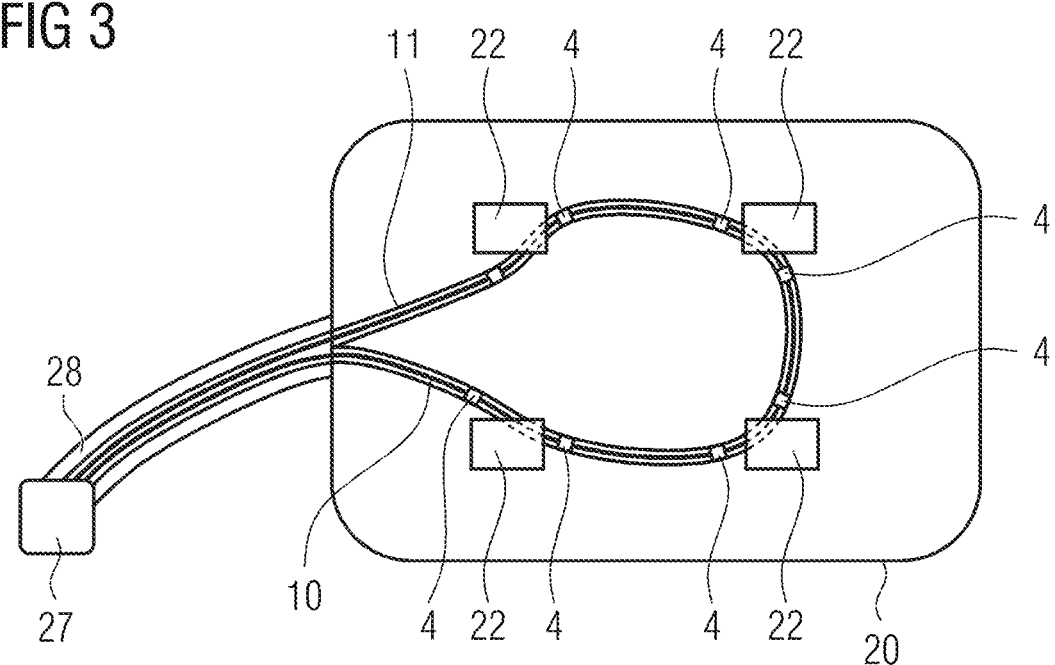
FIG. 3 shows a schematic representation of a local RF coil with several marker elements according to another embodiment of the invention.

FIG. 3 shows a schematic representation of a local RF coil 20 with several marker elements 4 according to another embodiment of the invention. In this embodiment, the marker elements 4 are fixed to a cable 10. The cable 10 may in particular be a pull rope. Preferably, the cable 10 or pull rope is guided by a hose or tube 11. In the state shown, the marker elements are within the scan range of the MRI system and are thus activated. The cable 10 inside the coil 20 and the coil cable 28 can be connected via a cable plug 27 to a cable part outside the coil 20. The cable part outside the coil 20 does not have marker elements 4 attached to it. Accordingly, the marker elements 4 can be pulled out of the coil 20 via the cable 10 such that there is only the part of the cable 10 without marker elements inside the coil 20 and the marker elements 4 can thus be deactivated by removing them from the coil via the cable 10. In order to activate the marker elements 4 again, they can be pulled back into the coil 20 to their predetermined position.

Figure 4:
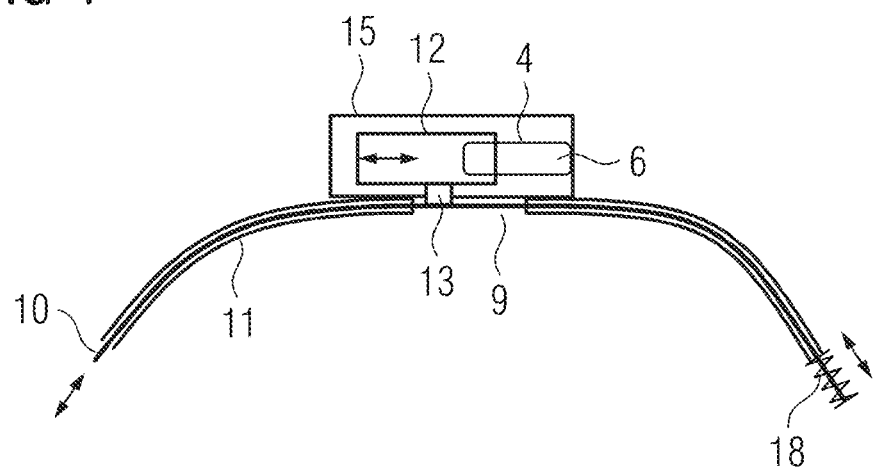
FIG. 4 shows a marker element with a shielding element according to an embodiment of the invention.

FIG. 4 shows a marker element 4 with a shielding element 12 according to an embodiment of the invention. The shielding element 12 is attached to a cable 10 that is guided via a tube 11. The tube 11 may preferably be flexible, e.g. be a hose. The tube 11 comprises an opening 9 and the cable 10 is fixed to the shielding element 12 via a gripping unit 13. The shielding element 12 can be pushed over a marker element 4 comprising an MR visible fluid 6 in order to deactivate the marker element 4 by shielding it and pulled away from the marker element 4 in order to activate it. The cable 10 is pretensioned by a non-magnetic spring 18 such that, if no additional force is applied to the cable 10, the shielding element 12 is naturally kept in a position where it shields the marker element 4. In this state the marker element is deactivated. In order to activate the marker element 4, the cable 10 can be pulled (to the left in the figure) such that the shielding element 12 is pulled (to the left) away from the marker element 4. Therein, the shielding element 12 is moved for a distance equivalent to the length of the marker element 4. The two directions of movement (towards the marker element and away from it) of the shielding element 12 are marked by an arrow. Both, the marker element 4 and the shielding element 12 are comprised within a housing 15, in particular a housing 15 made of plastic, which is configured to guide the shielding element 12 when the shielding element 12 is pulled by the cable 10. The marker element 4, on the other hand, is fixed to the housing 15. The marker element 4 may for example have a diameter of 1 mm two 20 mm and a length (along the direction of the arrow) of 1 mm to 50 mm. The shielding element 12 on the other hand has a similar or essentially equal geometry, wherein its inner walls are dimensioned such that a gap of about 0.1 mm to 0.5 mm exists between the shielding element and the marker element.

Figure 5:
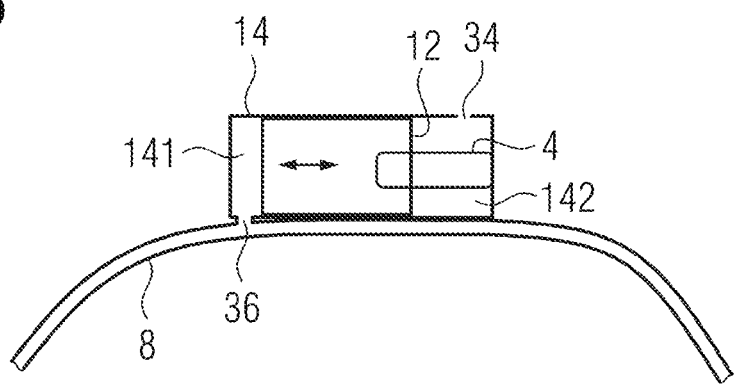
FIG. 5 shows a marker element with a shielding element according to another embodiment of the invention.

FIG. 5 shows a marker element 4 with a shielding element 12 according to another embodiment of the invention. In this embodiment, the shielding element 12 is moved via air pressure. The air pressure is provided via a fluid conducting element 8 which is connected to a first portion 141 of an air pressure chamber 14 via an air inlet 36 in an airtight manner. Within the air pressure chamber 14 there are a marker element 4 and the shielding element 12. The marker element is fixed to a wall of a second portion 142 of the air pressure chamber and the shielding element 12 is arranged between the first portion 141 and the second portion 142 of the air pressure chamber 14. In order to deactivate the marker element 4, the shielding element 12 can be pushed over the marker element 4 by providing a positive pressure (overpressure) in the first portion 141 via the fluid conducting element 8. Reversely, in order to activate the marker element 4, the shielding element 12 can be pulled away from the marker element 4 by providing a negative pressure (underpressure) in the first portion 141 via the fluid conducting element 8. The second portion comprises an air outlet (34) in order to ensure that the pressure in the second portion 142 can remain essentially constant, in particular remain at ambient pressure, to allow free movement of the shielding element 12 without creating counterpressure in the second portion 142 due to the movement of the shielding element 8.

Figure 6:
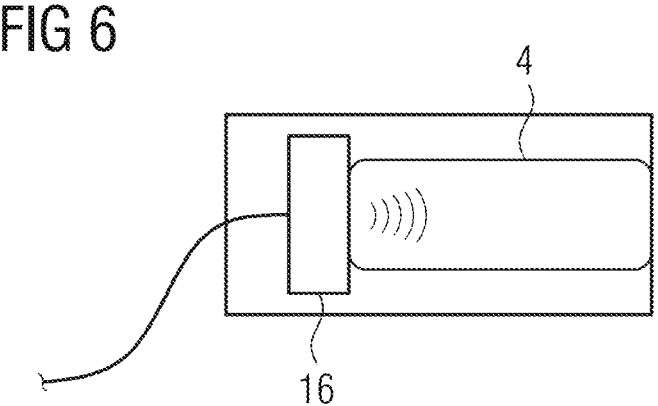
FIG. 6 shows a marker element with an ultrasound emitter according to an embodiment of the invention.

FIG. 6 shows a marker element 4 with an ultrasound emitter 16 according to an embodiment of the invention. The ultrasound emitter 16 is directly attached to the marker element 4. The marker element 4 can be deactivated via ultrasound waves created by the ultrasound emitter 16 by destroying the MR phase coherence of the marker element 4. Accordingly, the marker element 4 may be deactivated during an MRI measurement by the ultrasound waves. In order to localize the coil 20, the marker element 4 is activated by switching off the ultrasound emitter 16.

Figure 7:
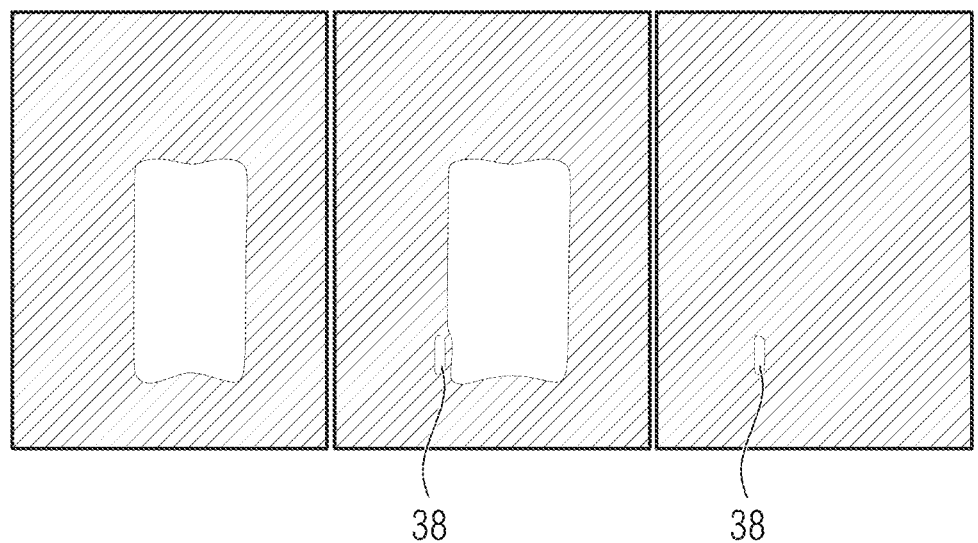
FIG. 7 shows MRI images used for localization of the coil via a marker element.

FIG. 7 shows MRI images used for localization of the coil 20 via a marker element 4. In the left picture, the marker element 4 was deactivated by shielding it with an RF shield and is thus not visible on the MRI image. In the centred picture, the marker element 4 was activated, i.e. not shielded, and thus appears as bright signal 38 in the MRI image. The right picture shows data, wherein the data of the left picture were subtracted from the data of the centred picture. Accordingly, the MRI image of the right picture only shows the bright signal 38 corresponding to the marker element 4. It is thus easier to determine the position of the marker element 4 within the field of view in order to determine the position of the coil 20, which is positioned at a predetermined position in relation to the marker element 4.

Figure 8:
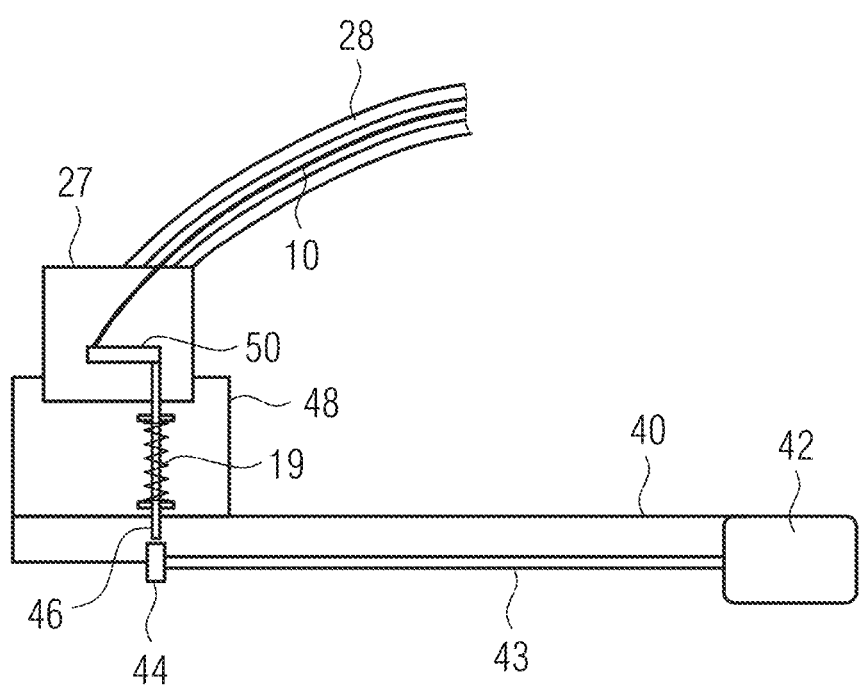
FIG. 8 shows a cable plug connected to a cable connector according to an embodiment of the invention.

FIG. 8 shows a cable plug 27 connected to a cable connector 48 according to an embodiment of the invention. This connection can in particular be used to move a shielding element 12 via a cable 10 which is guided through a coil cable 28 of a coil 20. In this embodiment, the MRI system comprises an MR compatible motor 42 which is configured to drive a rotary shaft 43 in order to rotate an eccentric 44. The motor 42, the rotary shaft and the eccentric 44 are located in or at a patient table 40. By rotating the eccentric, a bolt 43 within the cable connector 48 is pushed upwards against the force of a spring 19 thereby pushing a lever 50 inside the cable plug 27. The cable 10 is connected to the other end of the lever 50. As the lever 50 is pushed by the bolt 43 the cable 10 is pulled in the direction of the cable connector 48. The cable 10 is connected to a shielding element 12 (see FIG. 4) and by pulling the cable 10, the shielding element 12 is pulled away from the marker element 4 thereby activating the marker element 4. When the eccentric 44 is rotated further, the bolt 46 is no longer pushed by the eccentric 44 and is therefore pulled back by the spring 19 such that the lever 50 can also move back into its original position. Accordingly, the shielding element 12, for example due to the force of a further spring 18 inside the coil 20 as shown in FIG. 4, can move over the marker element 4 and thus deactivate the marker element 4.

FIG. 9 shows a fluid plug 26 connected to a tube connector 49 according to an embodiment of the invention. The connection is in particular configured to allow the transfer of air into the fluid conducting element 8 of the coil 20. Therefore, the tube connector 49 comprises an air socket 54 which is configured such, that the fluid plug of the coil 20 can be engage with the tube connector 49 thereby joining together the fluid conducting element 8 parts of the coil 20 and of the patient table 40. The configuration according to this embodiment may in particular be used to drive the shielding element 12, e.g. as shown in FIG. 5.

FIG. 10 shows a fluid plug 26 connected to a tube connector 49 according to another embodiment of the invention. This configuration may in particular be used for an embodiment where the marker element 4 is an MR visible liquid 6 guided inside a fluid conducting element 8, e.g. for the embodiment shown in FIG. 2, or for an embodiment wherein cooling liquid is guided into the coil 20. In addition to the embodiment of the fluid plug 26 and tube connector 49 as shown in FIG. 9 this embodiment has additional locking means. These are particularly useful in this case because a higher pressure may be needed to guide the MR visible liquid 6 as compared to guiding air and it is to be avoided that the MR visible liquid 6 might leak out when disconnecting the fluid plug 26. The tube connector and/or the fluid plug 26 comprise an unlocking button 56 which needs to be pushed before disconnecting the fluid plug 26. The fluid pump 52 is configured to pump the MR visible liquid out of the part of the fluid conducting element 8 that is located within the coil cable 28 and the coil 20. Until the MR visible fluid 6 has been removed from the coil 20 and coil cable 28, a locking element 58 is configured to ensures that a locking bolt 59 prevents removal of the fluid plug 26. After pumping the MR visible fluid 6 out of the coil 20 and coil cable 28, the locking bolt is pulled back and the fluid plug 26 can be removed.

Figure 11:
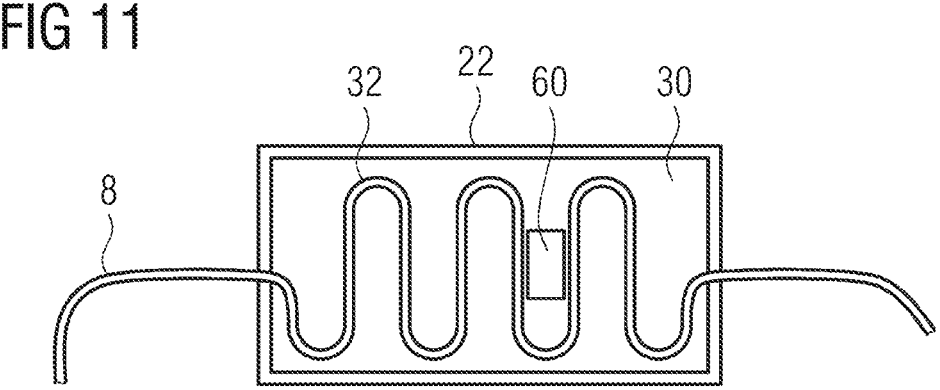
FIG. 11 shows an electronic component with a ceramic element according to an embodiment of the invention.

FIG. 11 shows an electronic component 22 of a coil 20 with a ceramic element 30 according to an embodiment of the invention. In this embodiment, the MR visible fluid 6 also serves as a cooling liquid. The electronic component 22 is encased in the ceramic element 30 which comprises a fluid channel 32 that is part of the fluid conducting element 8. The electronic component 22 is cooled by the MR visible fluid 6 via the ceramic element 30. In order to control the temperature of the electronic component 22, a temperature sensor 60 is arranged within or at the electronic component 22.

Figure 12:
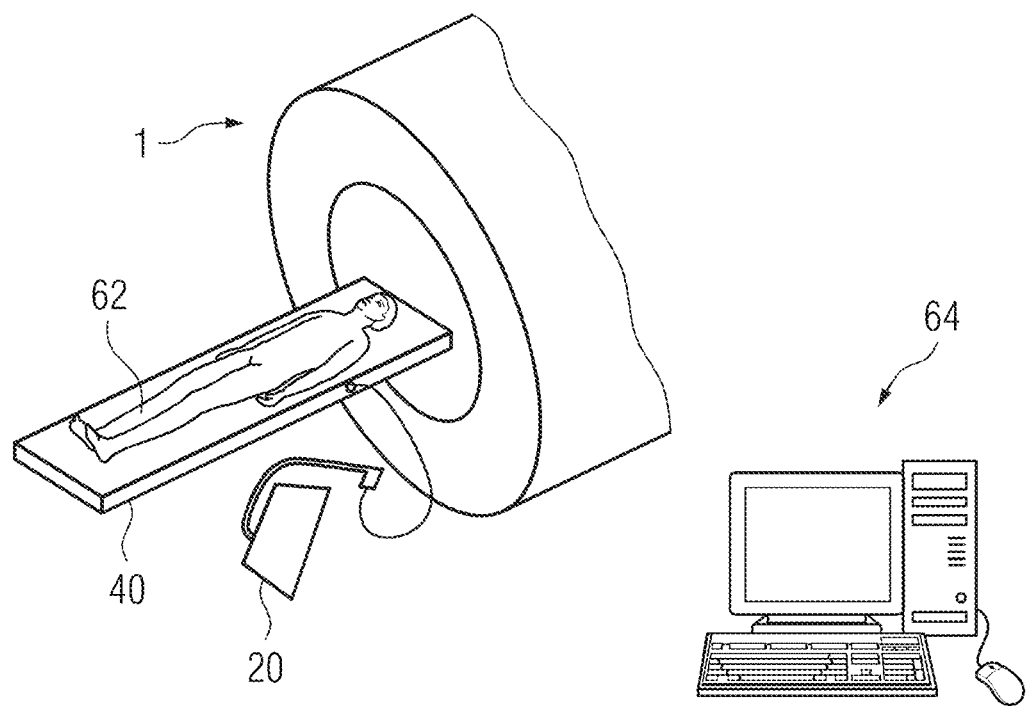
FIG. 12 shows a magnetic resonance imaging system according to an embodiment of the invention.

FIG. 12 shows a magnetic resonance imaging system 1 according to an embodiment of the invention. The system 1 comprises a patient table 40 on which a patient may lie during an examination and a coil 20 comprising the inventive marker element 4. A diagnostic measurement, a localization of the coil 20 and/or an attenuation correction can be controlled and/or carried out by a control unit 64.

Figure 13:
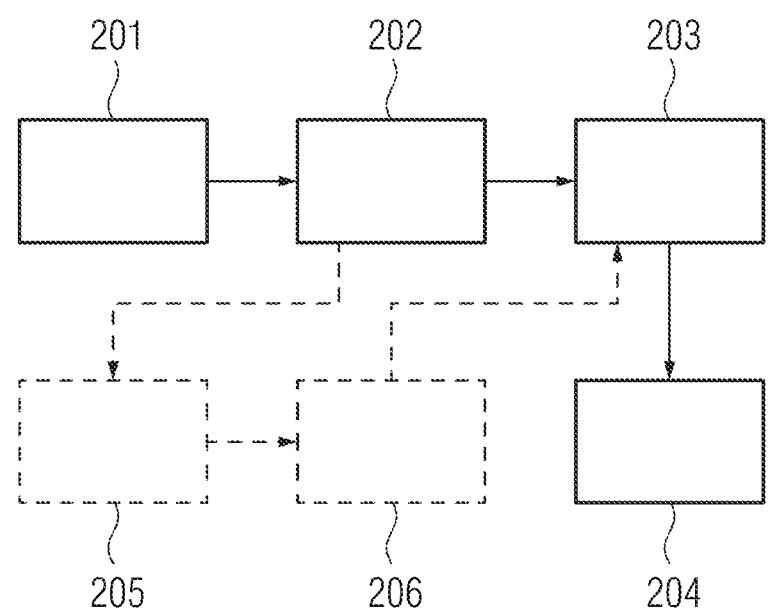
FIG. 13 shows a flow diagram of a method according to an embodiment of the invention.

FIG. 13 shows a flow diagram of a method according to an embodiment of the invention. In a first step 201 a marker element 4 is provided at a predetermined position relative to a coil in an activated state. Then, in a next step 202 a magnetic resonance measurement is taken with the magnetic resonance imaging system while the marker element is activated in order to obtain first test data. In a further step 203 the position of the marker element and thereby the position of the at least one coil is determined based on the first test data, in particular at the control unit. In a last step 204 the marker element is deactivated for further MRI measurements. Optionally there may be additional steps, wherein in step 205 a magnetic resonance measurement may be taken with the MRI system when the marker element is deactivated in order to obtain second test data. In step 206 the second test data may be subtracted from the first test data in order to obtain adjusted data, which are then used in step 203 instead of the test data for the localization of the coil 20.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'interface' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion.

In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing system or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CDROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

We claim:

1. A magnetic resonance imaging system comprising:
   at least one local radio frequency (RF) coil;
   at least one marker element, the magnetic resonance imaging system is being configured to activate the at least one marker element and deactivate the at least one marker element such that
      the at least one marker element is detectable by the magnetic resonance imaging system at a position relative to the at least one local RF coil based on the at least one marker element being activated, and
      the at least one marker element is not detectable by the magnetic resonance imaging system based on the at least one marker element being deactivated; and
   a shielding element, at least one of
      (i) the shielding element being movable into a first shielding position and into a first non-shielding position, or
      (ii) the at least one marker element being movable into a second shielding position and into a second non-shielding position,
   wherein
      the shielding element is configured to enclose the at least one marker element such that the at least one marker element is shielded from the magnetic resonance imaging system based on at least one of the shielding element being in the first shielding position or the at least one marker element being in the second shielding position, and
      the shielding element is configured to be apart from the at least one marker element such that the at least one marker element is detectable by the magnetic resonance imaging system based on at least one of the shielding element being in the first non-shielding position or the at least one marker element being in second the non-shielding position.

2. The magnetic resonance imaging system of claim 1, wherein the at least one marker element is a capsule containing a magnetic resonance visible fluid.

3. The magnetic resonance imaging system of claim 1, wherein the shielding element is a tube.

4. The magnetic resonance imaging system of claim 1, further comprising:
   an air pressure chamber; and
   a fluid conducting element connected to the air pressure chamber,
   wherein
      the shielding element and the at least one marker element are inside the air pressure chamber, and
      the shielding element is movable by air pressure provided via the fluid conducting element.

5. The magnetic resonance imaging system of claim 1, further comprising:
  a cable mechanism configured to move the shielding element between the first shielding position and the first non-shielding position.

6. The magnetic resonance imaging system of claim 1, further comprising:
  an ultrasound emitter configured to provide ultrasound waves at the at least one marker element to deactivate the at least one marker element with the ultrasound waves.

7. The magnetic resonance imaging system of claim 1, further comprising:
  a cable mechanism configured to
    activate the at least one marker element, and
    deactivate the at least one marker element.

8. The magnetic resonance imaging system of claim 7, further comprising:
  a hauling mechanism configured to move the at least one marker element to activate the at least one marker element and deactivate the at least one marker element, the hauling mechanism being configured to move the at least one marker element at least one of
    with respect to the at least one local RF coil, or
    in and out of a detectable area of the magnetic resonance imaging system.

9. The magnetic resonance imaging system of claim 1, further comprising:
  a hauling mechanism configured to move the at least one marker element to activate the at least one marker element and deactivate the at least one marker element, the hauling mechanism being configured to move the at least one marker element at least one of
    with respect to the at least one local RF coil, or
    in and out of a detectable area of the magnetic resonance imaging system.

10. The magnetic resonance imaging system of claim 9, wherein the hauling mechanism comprises:
  a movable cable extending from the at least one local RF coil to an area outside of the detectable area, the at least one marker element being attached to the movable cable such that the at least one marker element is movable between the at least one local RF coil and the area outside of the detectable area via the movable cable.

11. The magnetic resonance imaging system of claim 1, wherein
  the at least one marker element comprises a magnetic resonance visible fluid; and
  the magnetic resonance visible fluid has a magnetic resonance relaxation time below 1000 ms.

12. The magnetic resonance imaging system of claim 11, further comprising:
  a relocation system, the relocation system including:
    a fluid conducting element containing the magnetic resonance visible fluid, the fluid conducting element including a first part and a second part, the first part being at the at least one local RF coil or within the at least one local RF coil, and the second part being outside of a detectable area of the magnetic resonance imaging system, and
    a fluidic pump configured to move the magnetic resonance visible fluid between the first part and the second part.

13. The magnetic resonance imaging system of claim 11, further comprising:
  a cable mechanism configured to
    activate the at least one marker element, and
    deactivate the at least one marker element.

14. The magnetic resonance imaging system of claim 11, further comprising:
  a hauling mechanism configured to move the at least one marker element to activate the at least one marker element and deactivate the at least one marker element, the hauling mechanism being configured to move the at least one marker element at least one of
    with respect to the at least one local RF coil, or
    in and out of a detectable area of the magnetic resonance imaging system.

15. The magnetic resonance imaging system of claim 11, further comprising:
  a relocation system configured to
    relocate the at least one marker element with respect to at least one of
      the at least one local RF coil, or
      the magnetic resonance imaging system,
    deactivate the at least one marker element by removing the at least one marker element from at least one of
      the at least one local RF coil, or
      a field of view of the magnetic resonance imaging system, and
    activate the at least one marker element by moving the at least one marker element.

16. The magnetic resonance imaging system of claim 15, wherein the relocation system comprises:
  a fluid conducting element containing the magnetic resonance visible fluid, the fluid conducting element including a first part and a second part, the first part being at the at least one local RF coil or within the at least one local RF coil, and the second part being outside of a detectable area of the magnetic resonance imaging system; and
  a fluidic pump configured to move the magnetic resonance visible fluid between the first part and the second part.

17. The magnetic resonance imaging system of claim 16, wherein
  the at least one local RF coil includes at least one ceramic element around at least one electronic component of the at least one local RF coil;
  the at least one ceramic element includes at least one fluid channel connected to the fluid conducting element;
  the magnetic resonance visible fluid is a cooling fluid; and
  the fluidic pump is configured to move the magnetic resonance visible fluid through the at least one fluid channel.

18. A magnetic resonance imaging system comprising:
  at least one local radio frequency (RF) coil;
  at least one marker element, the magnetic resonance imaging system being configured to activate the at least one marker element and deactivate the at least one marker element such that
    the at least one marker element is detectable by the magnetic resonance imaging system at a position relative to the at least one local RF coil based on the at least one marker element being activated, and
    the at least one marker element is not detectable by the magnetic resonance imaging system based on the at least one marker element being deactivated; and
  a cable mechanism configured to
    activate the at least one marker element, and
    deactivate the at least one marker element.

19. A magnetic resonance imaging system comprising:
at least one local radio frequency (RF) coil;
at least one marker element, the magnetic resonance imaging system being configured to activate the at least one marker element and deactivate the at least one marker element such that
the at least one marker element is detectable by the magnetic resonance imaging system at a position relative to the at least one local RF coil based on the at least one marker element being activated, and
the at least one marker element is not detectable by the magnetic resonance imaging system based on the at least one marker element being deactivated; and
a hauling mechanism configured to move the at least one marker element to activate the at least one marker element and deactivate the at least one marker element, the hauling mechanism being configured to move the at least one marker element at least one of
with respect to the at least one local RF coil, or
in and out of a detectable area of the magnetic resonance imaging system.

20. The magnetic resonance imaging system of claim 19, wherein the hauling mechanism comprises:
a movable cable extending from the at least one local RF coil to an area outside of the detectable area, the at least one marker element being attached to the movable cable such that the at least one marker element is movable between the at least one local RF coil and the area outside of the detectable area via the movable cable.

* * * * *